United States Patent [19]

Biedermann et al.

[11] Patent Number: 5,702,451
[45] Date of Patent: Dec. 30, 1997

[54] SPACE HOLDER, IN PARTICULAR FOR A VERTEBRA OR AN INTERVERTEBRAL DISK

[76] Inventors: Lutz Biedermann, AM Schäfersteig 8, 78048 VS-Villingen; Jürgen Harms, Vogesenstrasse 60, 76337 Waldbronn, both of Germany

[21] Appl. No.: 581,149

[22] Filed: Dec. 29, 1995

[30] Foreign Application Priority Data

Feb. 14, 1995 [DE] Germany ............... 195 04 867.9

[51] Int. Cl.⁶ .................................. A61F 2/44
[52] U.S. Cl. ........................... 623/17; 606/61
[58] Field of Search .................. 623/17, 16, 66; 606/66, 61

[56] References Cited

U.S. PATENT DOCUMENTS

| | | |
|---|---|---|
| 4,820,305 | 4/1989 | Harms et al. ............... 623/17 |
| 5,015,247 | 5/1991 | Michelson ............... 623/17 |
| 5,055,104 | 10/1991 | Ray ............... 623/17 |
| 5,192,327 | 3/1993 | Brantigan . |
| 5,571,192 | 11/1996 | Schonhoffer ............... 623/17 |

FOREIGN PATENT DOCUMENTS

| | | |
|---|---|---|
| 369 603 | 5/1990 | European Pat. Off. . |
| 517030 | 12/1992 | European Pat. Off. . |
| 529275 | 3/1993 | European Pat. Off. . |
| 566810 | 10/1993 | European Pat. Off. . |

*Primary Examiner*—David Isabella
*Attorney, Agent, or Firm*—George W. Neuner

[57] ABSTRACT

A space holder in particular for a vertebra or an intervertebral disk is provided. The space holder comprises a jacket (1) having apertures (9, 10) and a first and second edge (7, 8). The edge has circumferentially adjacent recesses (9, 10; 9', 10') each extending in direction towards the other edge and a stop provided at at least one of the edges spaced from the outer edge. In order to provide for an easy manufacture and operation of the space holder the stop is formed by a member (11, 13, 16, 22) having an outer contour corresponding to the inner contour of the jacket (1) and nose-like projections (15) for engaging the recesses (9, 10) are provided at those locations of the periphery of the stop which correspond to the recesses (9, 10; 9', 10').

15 Claims, 3 Drawing Sheets

SPACE HOLDER, IN PARTICULAR FOR A VERTEBRA OR AN INTERVERTEBRAL DISK

FIELD OF THE INVENTION

The invention relates to a space holder for use with a vertebra or an intervertebral disk.

BACKGROUND OF THE INVENTION

Such a space holder is disclosed for example in document EP-B-O 268 115. This space holder comprises a stop formed by a ring on its inner side spaced from the corresponding free end of the jacket. The ring is connected with the jacket by means of bolts. In a particular embodiment a base plate comprising openings is mounted on the ring.

It is the object of the invention to simplify the space holder and make it more universally applicable.

SUMMARY OF THE INVENTION

In accord with the present invention, a space holder is provided, in particular, a vertebra or an intervertebral disk. The space holder comprises a jacket having apertures and a first and second edge. The edge has circumferentially adjacent recesses, each extending in a direction toward the opposite edge and a stop member is provided at least at one of the edges at a distance from that edge. The stop member is formed having an outer contour corresponding to the inner contour of the jacket. The stop member has nose-like projections at locations along its periphery corresponding to the recesses. Thus, the projections can engage the recesses.

DESCRIPTION OF PREFERRED EMBODIMENTS

Further features and advantages of the invention will stand out from the description of embodiments with reference to the Figures.

Figure 1:
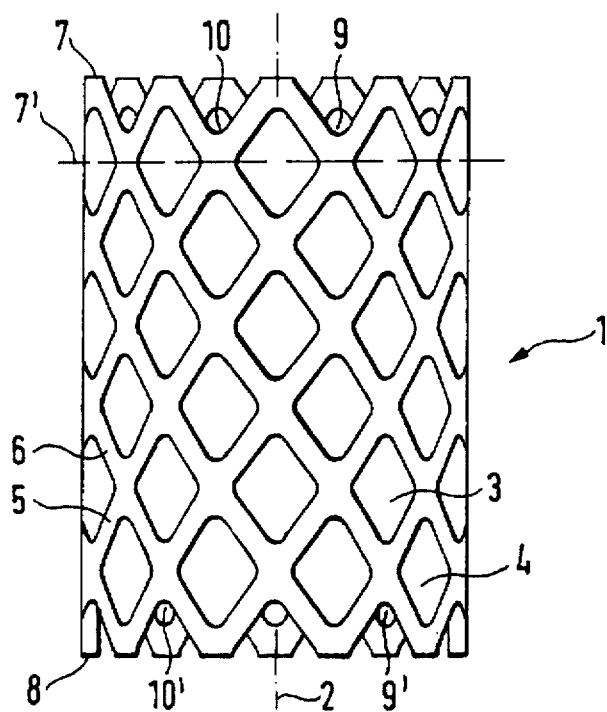
FIG. 1 is a side view of the jacket of the space holder.

As shown in particular in FIG. 1 the space holder comprises a closed jacket 1. The cross-section perpendicular to the longitudinal axis 2 of the jacket 1 is shaped in usual manner, in particular cylindrical, oval or kidneyshaped. In the manner shown in FIG. 1 the jacket 1 comprises diamond-shaped apertures 3, 4 having a longitudinal diagonal extending parallel to the jacket axis 2. Adjacent rows 3, 4 of such diamonds are mutually offset by half a diamond height. In this manner a grid is formed having webs 5, 6 intersecting at an acute angle and including equal angles with the longitudinal diagonal of the diamonds 3, 4. The upper edge 7 and the lower edge 8 both extend in a plane perpendicular to the longitudinal axis 2. The size of the diamonds 3, 4 and of the webs 5, 6 defining the diamonds is selected so that there is an integral number of diamonds in peripheral direction. The edges 7, 8 generate always an even number of V-shaped recesses 9, 10 or 9', 10', respectively, formed by the respective diamond base in peripheral direction. Owing to the above-described geometry the respective edge is quasi centrically symmetric to a point on the longitudinal axis 2 lying in the plane of the edge.

Figure 2:
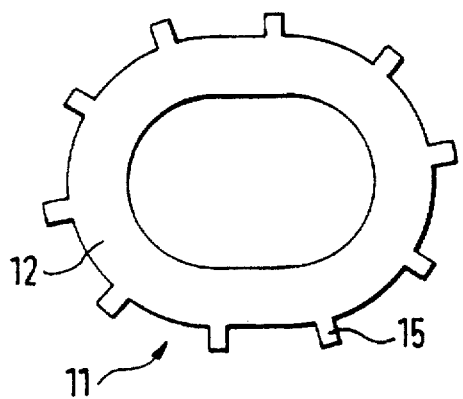
FIG. 2 is a top view of a first embodiment of the member to be connected with the jacket.

The first embodiment of a member 11 forming a stop shown in FIG. 2 is formed as a plate-shaped ring. The outer contour of the ring 12 corresponds to the inner contour of the jacket 1. Its dimensions are selected so that it can be pressed into the interior of the jacket but may also be pressed out again if desired, i.e. there is a frictional fit between the ring and the jacket 1. Equidistant projecting noses 15 are provided at the outer edge of the ring 12 in peripheral direction. The distance between two noses in peripheral direction equals the distance between two peripherally adjacent V-shaped recesses 9, 10. The cross-dimensions of the noses 15 in the plane of the plate are such that the noses fit smoothly into the base of the V-shaped recesses 9, 10. The length of the projecting noses corresponds to about the wall thickness of the associated jacket.

In use the Jacket 1 is brought to the desired length by severing the upper edge 7 and the lower edge. 8. Then one ring 12 is pressed into the interior of the jacket at the upper end and a second ring is pressed into the jacket interior at the lower end in such a manner that the noses 15 of the rings engage the corresponding basis of the associated V-shaped recesses 9, 10 and 9', 10', respectively.

Owing to the integral number of the V-shaped recesses and the central symmetry resulting therefrom one and the same member 11 may be used irrespective of the severing at the edge 7 or at the lowered edge 7' indicated in broken lines. If the edge is formed at the location 7' rather than at the location 7, then the ring 12 is inserted after rotation around its longitudinal axis, whereby using only one kind of rings the stock-keeping is reduced and the operation is simplified.

Figure 3:
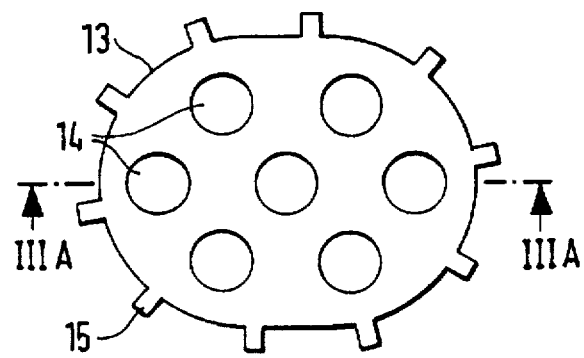
FIG. 3 is a top view of a second embodiment of the member.
Figure 3A:
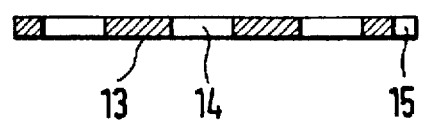
FIG. 3a is a sectional view along line IIIA—IIIA in FIG. 3.

FIG. 3 shows a member 13 of a modified embodiment. Again it is a plate wherein the holes are formed by bore-shaped holes 14 distributed over the plate. All further features correspond to the member 11.

Figure 4:
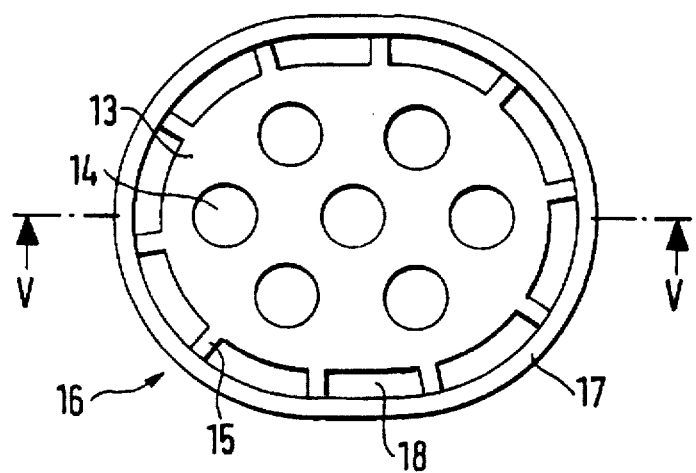
FIG. 4 is a top view of a third embodiment of the member.
Figure 5:
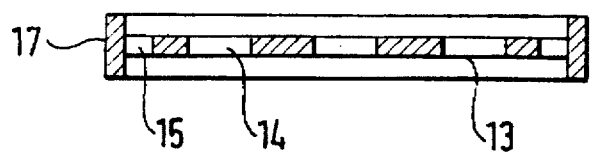
FIG. 5 is a sectioned lateral view along line V—V in FIG. 4.

The FIGS. 4 and 5 show a member 16 according to a third embodiment. This member again comprises a plate which corresponds to the embodiment shown in FIG. 3 as regards the holes 14 and the noses 15. An outer ring 17 is arranged around the plate. As best shown in FIG. 5, the outer ring has a ring wall extending perpendicular to the plane of the plate and therefore parallel to the outer surface of the jacket 1. The length of the noses 15 is selected so as to be longer than the thickness of the jacket 1 just by an amount to form a clearance 18 between the plate, the noses and the ring which allows pushing the member onto the corresponding free end 7, 8 of the jacket 1 to fit the noses 15 into the base of the respective corresponding V-shaped recesses 9, 10, 9', 10'. The inner surface of the ring 17 then sits close to the outer surface of the jacket 1.

Figure 6:
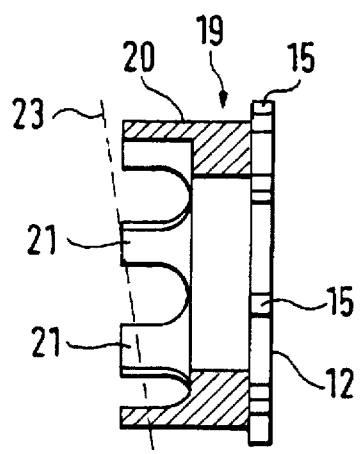
FIG. 6 is a sectional view along line VI—VI In FIG. 7 through a further modified embodiment.
Figure 7:
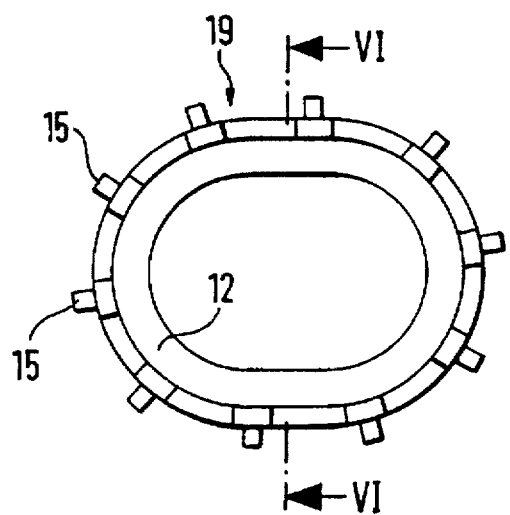
FIG. 7 is a top view of that embodiment.

In the FIGS. 6 and 7 a member 19 according to a further embodiment is shown. It has a plate-shaped ring 12 which is identical with the ring shown in FIG. 2. As best shown in FIG. 6 an edge portion 20 having an outer contour which corresponds to the inner contour of the jacket 1 is provided on one surface of this ring and the free end of the edge portion 20 opposite to the plate 12 has equidistant prongs 21 in circumferential direction. The height of the prongs 21 above the plate 12 is so that when inserted the prongs extend beyond the edge 7 or 8, resp., of the jacket 1 almost to their base.

Figure 8:
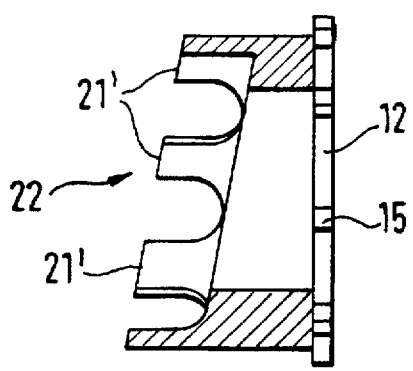
FIG. 8 shows a section along line VIII—VIII in FIG. 9.
Figure 9:
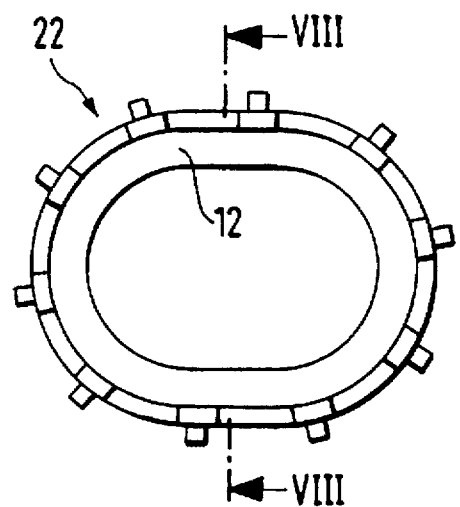
FIG. 9 is a top view of that further embodiment.

The embodiment of a member 22 shown in FIGS. 8 and 9 differs from the previously described embodiment only in that the base of the prongs is not in a plane parallel to the plate 12, but in a plane which is inclined with respect to the plate 12. The edge formed by the prongs lies also in a plane which is inclined with respect to the plate plane of the ring 12. The inclination is preferably between 8° and 10°.

Figure 10:
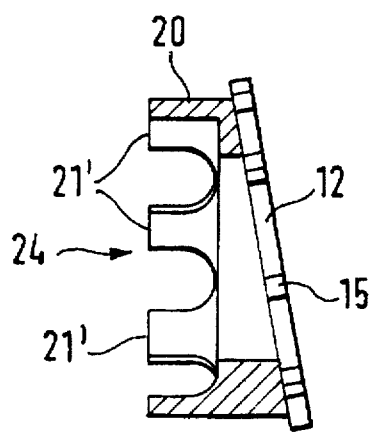
FIG. 10 shows a section along line X—X in FIG. 11.
Figure 11:
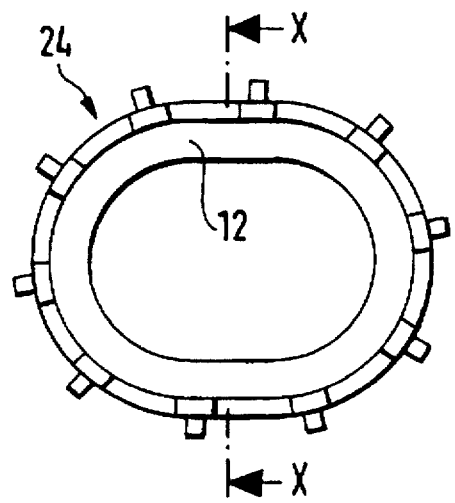
FIG. 11 is a top view of that further embodiment.

The embodiment of the member 24 shown in FIGS. 10 and 11 differs from the embodiment according to FIGS. 8 and 9 in that the edge portion 20 is inclined with respect to the plane of the plate, i.e. with an angle other than 90° with respect to the plate plane of the ring 12.

In operation both embodiments, i.e. the members 19 and 22, respectively, are inserted into the jacket in the same manner as the previously described embodiments so that the projecting noses 15 of the ring 12 lie in the lowermost parts of the V-shaped recesses 9, 10 and the prongs extend outwardly beyond the edge of the jacket. In the embodiment shown in FIGS. 6 and 7 the prongs 21 or 21' may be cut to different lengths, for example along the broken line 23 to form a wedge-shaped insert. Similarly the edge of the member 22 can be cut so that the predetermined angle between the outer edge and the plate-shaped ring 12 is varied. In this manner it is possible to obtain, using few basic members, space holders having different wedge angles.

The outer contour of the respective rings 12 and 13 is, of course, determined as a function of the respective inner contour of the associated jacket.

According to modifications of the above-described particularly preferred embodiments the recesses of the edge may have other shapes in place of the V-shape, for example U-shaped or slit-shaped recesses.

We claim:

1. Space holder for use with a vertebra or an intervertebral disk, the space holder comprising
a jacket member comprising a hollow sleeve having an inner contour, an upper first edge, a lower second edge and apertures provided in said jacket, adjacent recesses provided at said first and second edge, said recesses located along the circumference of one of said edges and extending towards an opposite edge, and stop means comprising a stop member having an outer contour corresponding to said inner contour of said jacket member and comprising nose-shaped projections being provided at locations of said periphery corresponding to said recesses for engaging said recesses of said jacket.

2. The space holder of claim 1, wherein said recesses comprise equidistant V-shaped recesses.

3. The space holder of claim 1, wherein said stop member comprises an outer periphery which is dimensioned for frictional fit of said stop member within said jacket member.

4. The space holder of claim 1, said jacket member comprising a grid having diamond-shaped apertures.

5. The space holder of claim 4, wherein each of said diamonds has a diagonal extending parallel to a longitudinal axis of said jacket member.

6. The space holder of claim 1, wherein said stop member comprises a plate member.

7. The space holder of claim 6, said plate member being configured as a ring.

8. The space holder of claim 6, said plate member comprising a plurality of adjacent holes.

9. The space holder of claim 6, said jacket member having a defined wall thickness and the said projections having a length which is at least equal to said wall thickness.

10. The space holder of claim 9 said projections having outer ends, an outer ring extending around said outer ends of said projections, said outer ring having a contour which corresponds to an outer contour of said jacket member.

11. The space holder of claim 10, wherein said outer ring comprises a rim having a thickness greater than the thickness of said plate member and is connected to said projections.

12. The space holder of claim 1, wherein said stop member has a serrated edge provided on that side of said stop member which is external to said jacket member.

13. The space holder of claim 12, wherein said serrated edge is in a plane that is parallel to said plate member.

14. the space holder of claim 12, wherein said serrated edge is in a plane that is oblique with respect to said plate member.

15. The space holder of claim 1, wherein said edge comprises an even number of equidistant recesses.

* * * * *